(12) United States Patent
Fisher et al.

(10) Patent No.: US 8,249,696 B2
(45) Date of Patent: Aug. 21, 2012

(54) SMART PEDICLE TOOL

(75) Inventors: Michael A. Fisher, Middleborough, MA (US); Paul Birkmeyer, Mashfield, MA (US); John Riley Hawkins, Cumberland, RI (US); Katherine Herard, South Boston, MA (US); Anwar Upal, Fall River, MA (US)

(73) Assignee: DePuy Spine, Inc., Raynham, MA (US)

( * ) Notice: Subject to any disclaimer, the term of this patent is extended or adjusted under 35 U.S.C. 154(b) by 1095 days.

(21) Appl. No.: 11/959,603

(22) Filed: Dec. 19, 2007

(65) Prior Publication Data

US 2009/0163901 A1 Jun. 25, 2009

(51) Int. Cl.
*A61B 6/00* (2006.01)

(52) U.S. Cl. ............. 600/476; 600/473; 606/2; 606/10; 606/13; 606/53; 606/60; 606/65; 606/297; 606/300

(58) Field of Classification Search .......... 600/472, 600/476, 473; 606/2, 10, 13, 53, 60, 65, 606/297, 300
See application file for complete search history.

(56) References Cited

U.S. PATENT DOCUMENTS

| | | | |
|---|---|---|---|
| 5,201,729 A | 4/1993 | Hertzmann et al. | |
| 5,259,380 A | 11/1993 | Mendes et al. | |
| 5,385,143 A | 1/1995 | Aoyagi | |
| 5,401,270 A | 3/1995 | Muller et al. | |
| 5,402,793 A * | 4/1995 | Gruner et al. | 600/447 |
| 5,445,608 A | 8/1995 | Chen et al. | |
| 5,447,159 A | 9/1995 | Schultz | |
| 5,596,992 A | 1/1997 | Haaland et al. | |
| 5,616,140 A | 4/1997 | Prescott | |
| 5,640,978 A | 6/1997 | Wong | |
| 5,792,053 A | 8/1998 | Skladnev et al. | |
| 5,800,350 A | 9/1998 | Coppleson et al. | |
| 5,800,478 A | 9/1998 | Chen et al. | |
| 5,948,008 A | 9/1999 | Daikuzono | |
| 5,987,346 A | 11/1999 | Benaron et al. | |
| 6,063,108 A | 5/2000 | Salansky et al. | |
| 6,073,051 A | 6/2000 | Sharkey et al. | |

(Continued)

FOREIGN PATENT DOCUMENTS

EP 1021223 A1 7/2000

(Continued)

OTHER PUBLICATIONS

Optical Properties of the Skull, Firbank M. Hiraoka, M. Essenpreis, M. Delpy, DT. Measurement of the optical properties of the skull in the wavelength range 650-950 nm. Physics in Medicine & Biology. 38(4):503-10, Apr. 1993.

(Continued)

*Primary Examiner* — James Kish
(74) *Attorney, Agent, or Firm* — Nutter McClennen & Fish LLP (57) ABSTRACT

Various methods and devices are provided for navigating through bone. In one embodiment, a bone navigation device is provided and includes a bone penetrating member configured to be implanted in bone and having at least one optical waveguide extending therethrough. The optical waveguide is adapted to illuminate tissue surrounding the device and to receive reflected/transmitted light from the tissue to determine the optical characteristics of the tissue, thus facilitating navigation through the tissue. At least one window can be formed in the bone penetrating member for allowing light from the at least one optical waveguide to illuminate the tissue, and for receiving the reflected light.

16 Claims, 8 Drawing Sheets

U.S. PATENT DOCUMENTS

| | | | |
|---|---|---|---|
| 6,214,012 | B1 | 4/2001 | Karpman et al. |
| 6,270,492 | B1 | 8/2001 | Sinofsky |
| 6,409,719 | B1 | 6/2002 | Manning |
| 6,494,882 | B1 | 12/2002 | Lebouitz et al. |
| 6,494,900 | B1 | 12/2002 | Salansky et al. |
| 6,503,269 | B2 | 1/2003 | Nield et al. |
| 6,516,209 | B2 | 2/2003 | Cheng et al. |
| 6,516,214 | B1 | 2/2003 | Boas |
| 6,537,304 | B1 | 3/2003 | Oron |
| 6,553,356 | B1 | 4/2003 | Good et al. |
| 6,577,884 | B1 | 6/2003 | Boas |
| 6,579,244 | B2* | 6/2003 | Goodwin ............ 600/561 |
| 6,587,703 | B2 | 7/2003 | Cheng et al. |
| 6,594,513 | B1 | 7/2003 | Jobsis et al. |
| 6,597,931 | B1 | 7/2003 | Cheng et al. |
| 6,611,833 | B1 | 8/2003 | Johnson |
| 6,628,809 | B1 | 9/2003 | Rowe et al. |
| 6,671,540 | B1 | 12/2003 | Hochman |
| 6,733,496 | B2 | 5/2004 | Sharkey et al. |
| 6,749,605 | B2 | 6/2004 | Ashley et al. |
| 6,816,605 | B2 | 11/2004 | Rowe et al. |
| 6,866,678 | B2 | 3/2005 | Shenderova et al. |
| 6,934,576 | B2* | 8/2005 | Camacho et al. ............ 600/473 |
| 7,131,963 | B1 | 11/2006 | Hyde |
| 7,465,313 | B2 | 12/2008 | DiMauro et al. |
| 2002/0002336 | A1 | 1/2002 | Marchitto et al. |
| 2002/0045922 | A1 | 4/2002 | Nield et al. |
| 2002/0087206 | A1 | 7/2002 | Hirschberg et al. |
| 2002/0138073 | A1 | 9/2002 | Intintoli et al. |
| 2003/0013936 | A1* | 1/2003 | Jackson, III ............ 600/104 |
| 2003/0092995 | A1 | 5/2003 | Thompson |
| 2003/0125782 | A1 | 7/2003 | Streeter |
| 2003/0143510 | A1* | 7/2003 | Berube-Lauziere et al. ... 433/29 |
| 2003/0225331 | A1 | 12/2003 | Diederich et al. |
| 2004/0111132 | A1 | 6/2004 | Shenderova et al. |
| 2005/0054900 | A1 | 3/2005 | Mawn et al. |
| 2005/0085910 | A1 | 4/2005 | Sweeney |
| 2005/0107800 | A1 | 5/2005 | Frankel et al. |
| 2005/0143732 | A1* | 6/2005 | Burch et al. ............ 606/53 |
| 2005/0171551 | A1 | 8/2005 | Sukovich et al. |
| 2005/0277923 | A1* | 12/2005 | Sweeney ............ 606/61 |
| 2006/0206172 | A1 | 9/2006 | DiMauro et al. |
| 2006/0235500 | A1* | 10/2006 | Gibson et al. ............ 607/137 |
| 2006/0271131 | A1 | 11/2006 | Passy et al. |
| 2006/0287695 | A1 | 12/2006 | DiMauro et al. |
| 2007/0049819 | A1 | 3/2007 | Stifter et al. |
| 2007/0073300 | A1 | 3/2007 | Attawia et al. |
| 2007/0073363 | A1 | 3/2007 | DiMauro et al. |

FOREIGN PATENT DOCUMENTS

| | | |
|---|---|---|
| WO | 0212854 | 2/2002 |
| WO | 2004026363 | 4/2004 |

OTHER PUBLICATIONS

Light Scattering, Takeuchi, Akira; Araki, Ryuichiro; Proskurin, S. G.; Takahashi, Yukari; Yamada, Yukio; Ishii, Jun; Katayama, Shigehiro; Itabashi, Akira. A New Method of Bone Tissue Measurement Based upon light Scattering. Journal of Bone & Mineral Research. 12(2):261-266, Feb. 1997.

Transmission Spectroscopy (Optical Biopsy) Pifferi A., Torricelli A., Taroni P., Bassi A., Chikoidze E., Giambattistelli E., Cubeddu R., Optical biopsy of bone tissue: a step toward the diagnosis of bone pathologies. Journal of Biomedical Optics. 9(3):474-80, May-Jun. 2004.

3D Optical Imaging (Clemson) Xu Y., Iftimia N., Jiang H., Key Ll, Bolster MB,. Three-dimensional diffuse optical tomography of bones and joints. Journal of Biomedical Optics. 7(1 ):88-92, Jan. 2002.

Microscope Spectroscopy (NY) Paschalis EP., Betts F. DiCarlo, E. Mendelsohn ,R. Boskey AL. FTIR microspectroscopic analysis of human iliac crest biopsies from untreated osteoporotic bone. Calcified Tissue International. 61(6):487-92, Dec. 1997.

International Search Report, Jun. 1, 2009, PCT/US2008/084599.

Akai, Laser's effect on bone and cartilage chance induced by joint immobilization: an experiment with animal model, Laser Surg Med., 1997, pp. 480-484, vol. 21(5).

Ariga, Mechanical stress-induced apoptosis of endplate chondrocytes in organ-cultured mouse intervertebral discs, Spine, 2003, pp. 1528-1533, vol. 28(14), Lippincott Willian & Wilkins, Inc.

Bai, Augmentation of Anterior Vertebral Body Screw Fixation by an Injectable, Biodegradable Calcium Phosphate Bone Substitute; Spine, 26(24) 2679-83.

Bayat, Effect of low-power helium-neon laser irradiation on 13-week immobilized articular cartilage of rabbits, Indian J Exp Biol., 2004, pp. 866-860, vol. 42(9).

Bjordal, A systematic review of low level laser therapy with location-specific doses for pain from chronic joint disorders, Australian Journal of Physiotherapy, 2003, pp. 107-116, vol. 49.

Borenstein, Epidemiology, etiology, diagnostic evaluation and treatment of low back pain, Curr Opin Rheumatol, 1999, pp. 15-17, vol. 11(2).

Bossy, in vitro survey of low energy laser beam penetration in compact bone, Acupunct Electrother Res., 1985, pp. 35-39, vol. 10(1-2).

Carnevalli, Laser light prevents apoptosis in Cho K-1 cell line, J Clin Laser Med Surg, 2003, pp. 193-6, vol. 21(4), Mary Ann Lieber, Inc.

Cho, Effect of low-level laser therapy on Osteoarthropathy in Rabbit, in Vivo, 2004, pp. 585-592, vol. 18.

Cook, Biomechanical study of pedicle screw fixation in severely osteoporotic bone; Spine Journal, 4 (2004) 402-8.

Cook, Lumbosacral fixation using expandable pedicle screws: an alternative in reoperation and osteoporosis; Spine Journal, 1(2001) 109-114.

Del Carlo, Nitric oxide-mediated chondrocyte cell death requires the generation of additional reactive oxygen species, Arthritis Rheum., 2002, pp. 394-403, vol. 46(2).

Dortbudak, Effect of low-power laser irradiation on bony implant sites; Clin. Oral Implants Res., 2002, Jun. 13(3) 288-92.

Ebert, Effect of irradiation with a low-intensity diode laser on the metabolism of equine articular cartilage in vitro, Am J Vet Res., 1998, pp. 1613-1618, vol. 59(12).

Guzzardella, Assessment of low-power laser biostimulation on chondral lesions: an "in vivo" experimental study, Artif Cells Blood Substit Immobil Biotechnol., 2000, pp. 441-449, vol. 28(5).

Guzzardella, Cartilage cell stimulation with low-power laser: experimental assessment, 1999, pp. 43-47, vol. 70 (3-4).

Guzzardella, Laser stimulation on bone defect healing: an in vitro study, Lasers Med Sci., 2002, pp. 216-220, vol. 17(3).

Guzzardella, Laser Technology in Orthopedics: Preliminary Study on Low Power Laser Therapy to Improve the Bone-Biomaterial Interface; Int. J. Artif. Organs, Dec. 24, 2001,(12): 898-902.

Guzzardella, Low-power diode laser stimulation of surgical osteochondral defects: results after 24 weeks, Artif Cells Blood Substit Immobil Biotechnol., 2001, pp. 235-244, vol. 29(3).

Hamajima, Effect of low-level laser irradiation on osteoglycin gene expression in osteoblasts Laser Med Sci 2003 vol. 18 (2) pp. 78-82.

Herman, In vitro effects of Nd:YAG laser radiation on cartilage metabolism, J Rheumatol, 1988, pp. 1818-26, vol. 15 (12).

Iwatsuki, The effect of laser irradiation for nucleus pulposus: an experimental study, Neruol Res, 2005, pp. 319-323, vol. 27(3), W. S Maney & Son.

Jia, Effect of low-power he-ne laser irradiation on rabbit articular chondrocytes in vitro, Lasers in Surgery and Medicine, 2004, pp. 323-328, vol. 34, Wiley-Liss, Inc.

Jouzeau, Nitric oxide (NO) and cartilage metabolism: NO effects are modulated by superoxide in response to IL-1, Biorheology, 2002, pp. 201-214, vol. 39(1-2).

Khandra, Effect of LLLT on Implant-tissue Interaction; Swed. Dent. J. Suppl., 2005, (172) 1-63.

Khandra, Laser Therapy Accelerates Initial Attachment and Subsequent Behaviour of Human Oral Fibriblasts Cultured on Titanium Implant Material; Clin Oral Implants Res. Apr. 16, 2005,(2) 168-75.

Khandra, Low-level Laser Therapy Stimulates bone-Implant Interaction: An Experimental Study in Rabbits; Clin. Oral Implants Res., Jun. 2004,:15(3):325-332.

Khanna, Augmentation of the expression of proangiogenic genes in cardiomyocytes with low dose laser irradiation in vitro, Cardiovasc Radiat Med., 1999, pp. 265-269, vol. 1(3).

Kipshidze, Low-power helium: neon laser irradiation enhances production of vascular endothelial growth factor and promotes growth of endothelial cells in vitro, Lasers Surg Med, 2001, pp. 355-364, vol. 28(4).

Kolari, Poor penetration of infra-red and helium neon low poser laser light into the dermal tissue, Acupunct Electrother Res., 1993, pp. 17-21, vol. 18(1).

Kolarova, Penetration of the laser light into the skin in vitro, Lasers Surg Med., 1999, pp. 231-235, vol. 24(3).

Lin, Effects of helium-neon laser on levels of stress protein and arthritic hist, Am J. Phys Med Rehabil, 2004, pp. 758-765, vol. 83(10), Lippincott, Williams & Wilkins.

Lopes, Infrared Laser Light Reductes Loading Time of Dental Implants: A Raman Spectroscopic Study; Photomed. Laser Surg. Feb. 2005 23(1) 27-31.

Matsushuta, Hypoxia-induced nitric oxide protects chondrocytes from damage by hydrogen peroxide, Inflamm Res., 2004, pp. 344-350, vol. 53(8). Epub Aug. 2004.

Morrone, Biostimulation of human chondrocytes with Ga-Al-As diode laser:'in vitro', Artif Cells Blood Substit Immobil Biotechnol, 2000, pp. 193-201, vol. 28(2).

Nerlich, 1997 Volvo Award winner in basic science studies. Immunohistologic markers for age-related changes of human lumbar intervertebral discs, 1997, pp. 2781-1795, vol. 22(24).

Notzli, Laser Doppler flowmetry for bone blood flow measurements: helium-neon laser light attenuation and depth of perfusion assessment, J Orthop Res., 1989, pp. 13-424, vol. 7(3).

Pullin, Effects of holmium: YAG laser energy on cartilate metabolism, healing and biochemical properties of lesional and perilesional tissue in a weight-bearing model, Arthroscopy, 1996, pp. 15-25, vol. 12(1).

Rannou, Intervertebral Disc Degeneration, American Journal of Pathology, 2004, pp. 915-924, vol. 164(3), American Society for Investigative Pathology.

Reed, An in vivo study of the effect of excimer laser irradiation on degenerate rabbit articular cartilage, Arthroscopy, 1994, pp. 78-84, vol. 10(1).

Schemitsch, Evaluation of a laser Doppler flowmetry implantable fiber system for determination of threshold thickness for flow detection in bone, Calcif Tissue Int., 1994, pp. 216-222, vol. 55(3).

Schultz, Effects of varying intensities of laser energy on articular cartilage: a pr, Laser Surg Med, 1958, pp. 577-88, vol. 5(6).

Shefer, Low-energy laser irradiation promotes the survival and cell cycle entry of skeletal muscle satellite cells, Journal of Cell Science, 2002, pp. 1461-1469, vol. 115, The Company of Biologists Ltd.

Spivak, The effect of low-level Nd:YAG laser energy on adult articular cartilage in vitro, Arthroscopy: The Journal of Arthroscope and Related Surgery, 1992, pp. 36-43, vol. 8(1), Raven Press Ltd.

Torricelli, Laser biostimulation of cartilage: in vitro evaluation, Biomed Pharmacother, 2001, pp. 117-20, vol. 55.

Wang, Measuring dynamics of caspase-3 activity in living cells using FRET technique during apoptosis induced by high fluence low-power laser irradiation, Lasers Surg Med., 2005, pp. 2-7, vol. 36(1).

Wong-Riley, Photobiomodulation directly benefits primary neurons functionally inactivated by toxins, J Biol Chem, 2005, pp. 4761-71, vol. 280(6).

Wong-Riley,Light-emitting diode treatment reverses the effect of TTX on cytochrome oxidase in neurons, Neuroreport, 2001, pp. 3033-3037, vol. 12(14).

\* cited by examiner

SMART PEDICLE TOOL

FIELD

The present application relates to devices and methods for navigating through bone to determine the optical characteristics of the bone.

BACKGROUND

Various devices are inserted into the body during a variety of surgical procedures. Often, these devices must be inserted into a specific type of tissue, such as bone, and into a specific location within the tissue in order to achieve a desire result. For example, often a certain type of bone is more desirable for implantation for a number of reasons, such as the strength and location of that type of bone. It is also important for a surgeon to be able to detect a bone breach during implantation of a device into bone.

Specific to spinal surgery, screws are mounted in the vertebral bodies using the pedicles. The pedicles are columns of cancellous bone surrounded by a cortical shell. Placement of a spinal pedicle screw with a trajectory that is not aligned with the major axis of the pedicle or is placed too close to the cortical shell can result in breach of the pedicle and potential exposure, irritation, or damage to the local neural ganglia that exit through the foraminal openings defined between superior and inferior pedicles. Also, insertion of a screw that is significantly larger than the prepared hole is liable to fracture or split the pedicle, thus exposing the nerve ganglia to potential mechanical or chemical irritation and trauma. Screw misplacement rates in modern spinal surgery range from 0 to 40% of all screws placed with placement of thoracic screws having the highest potential for complications.

Currently techniques include the use of fluoroscopic imaging to visualize placement of components into bone. While useful, this technique has several shortcomings, including poor visualization of complex bone anatomies and geometric relationships between different types of bone, such as the complexities of the spinal column. Evoked muscular electromyograms are also used, which electrically stimulate the device implanted into bone to cause the nerves within the breached bone to be stimulated and thereby result in a muscular response. Problems with this technique include the fact that small bone breaches usually go undetected, and can fail to stimulate nerves that have been exposed or compressed during the procedure.

Accordingly, there remains a need for improved methods and devices for local surgical navigation in bone, and in particular, there remains a need for methods and devices for determining the composition of bone to be used for the implantation of devices into bone.

SUMMARY

Various methods and devices for navigation of bone using local tissue spectroscopy are provided. In one embodiment, a bone navigation device is provided and includes a bone penetrating device adapted to penetrate bone and having at least one optical waveguide extending therethrough and configured to emit light in the visible to near infrared range. The optical waveguide is configured to illuminate bone and to receive reflected light from the bone to determine the optical characteristics of the bone. At least one window can be formed in the bone penetrating device and adapted to allow light from the at least one optical waveguide to illuminate the bone. In one exemplary embodiment, the device can include first and second optical waveguides. The first optical waveguide can be configured to illuminate bone and the second optical waveguide can be configured to receive light reflected from the illuminated bone. Alternatively, a single waveguide can be used to both illuminate bone and receive light. In one embodiment, the optical waveguide can be an optical fiber.

The bone navigation device can also include additional features adapted to facilitate navigation through bone. In one embodiment, the bone navigation device can include a processor coupled to the optical waveguide(s) and configured to collect data from the optical waveguide(s) for determining the optical characteristics of bone from which the light is reflected. The bone navigation device can further include a signaling mechanism disposed on the bone penetrating device and configured to provide distinct signals based on the determined optical characteristics of the bone.

The bone penetrating device can be in the form of a variety of devices adapted to penetrating bone. For example, the bone penetrating device can be a bone tap, drill, or awl, an implant, such as a bone screw, a bone vibratome blade, a surgical probe, a cannula, or various other tools and implants that are inserted into bone. A person skilled in the art will appreciate that this list is merely exemplary and that a variety of other devices can be used to form the bone penetrating device.

Methods for navigating bone are also provided, and in one embodiment the method can include driving a bone penetrating device into bone, illuminating tissue surrounding the bone penetrating device with light from at least one optical waveguide extending through the bone penetrating device, detecting light reflected back from the tissue to determine the optical characteristics of the tissue, and navigating through the bone based on the optical characteristics of the tissue. Determining the optical characteristics of the tissue can include comparing the wavelength of light reflected back from the tissue with known values indicating tissue composition. For example, determining the composition of the tissue can include determining whether the tissue is cortical bone, bone marrow, trabecular bone, soft tissue, neural tissue, or non-bone tissue.

The bone penetrating device can be moved to a variety of locations surrounding the bone to determine the optical characteristics at these locations. For example, the method can include repositioning the bone penetrating device axially to determine the composition of tissue, such as bone, at a plurality of depths, and/or repositioning the bone penetrating device radially to determine the composition of tissue at a plurality of locations axially surrounding the bone penetrating device. In one exemplary embodiment, a signal can be generated that indicates a portion of the bone into which the component can be implanted, and/or a warning signal can indicate a portion of the bone into which the component cannot be implanted. This can be accomplished in a variety of ways. For example, the bone penetrating device can include an LED that can be illuminated to deliver the signal. In one embodiment, once the optical characteristics of the tissue are determined, the method can also include implanting a component into the bone based on the determined optical characteristics of the tissue at a desired location.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for navigating through bone based on characteristics of reflected light received therefrom. In general, a bone navigation device is provided that is configured to illuminate tissue, including bone, surrounding the device using at least one optical waveguide extending through a bone penetrating member. The optical waveguide(s) is also adapted to receive reflected light from the tissue surrounding the device. The optical characteristics of the reflected light can be measured and compared to the known spectral characteristics of the delivered light to determine its composition. Different tissues have different absorption characteristics. For example, bone reflects most wavelengths of light whereas marrow reflects mostly red wavelengths. The differences in absorption spectra between bone types, as well as other types of tissue, can be used to discriminate one bone from another, as well as from other types of tissue. Accordingly, once the optical characteristics of the bone has been determined, this information can be used for placement of components into the bone in appropriate locations, or for various other purposes.

FIGS. 1A-3C illustrate various exemplary embodiments of a device for navigating bone. FIGS. 1A-E illustrate one exemplary embodiment of a bone navigation system 10 that generally includes a bone navigation device 11 having a bone penetrating member 12 extending from a handle 14 and having a tip adapted to penetrate bone. At least one optical waveguide 18 can extend through the bone penetrating member 12 to the tip and can be adapted to illuminate tissue through a window 20 formed in the tip, and to collect light reflected from the illuminated tissue. A person skilled in the art will appreciate that the optical waveguide can have a variety of forms, including an optical fiber or any optical conduit. The bone navigation system 10 can also include an optical spectroscope and computer for analyzing the reflected light and determining the optical characteristics of the illuminated tissue.

Figure 1A:
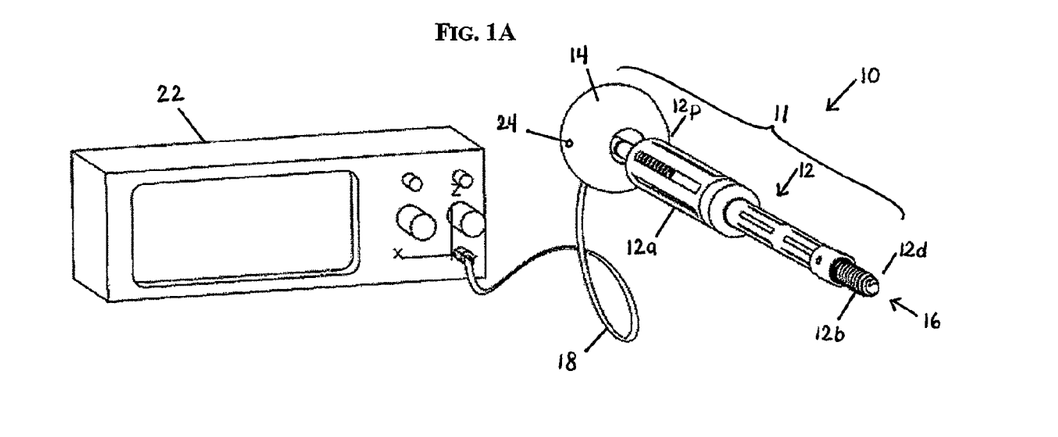
FIG. 1A is a perspective view of one embodiment of a bone navigation device having a bone penetrating device in the form of a cannulated bone screw and driver.
Figure 1B:
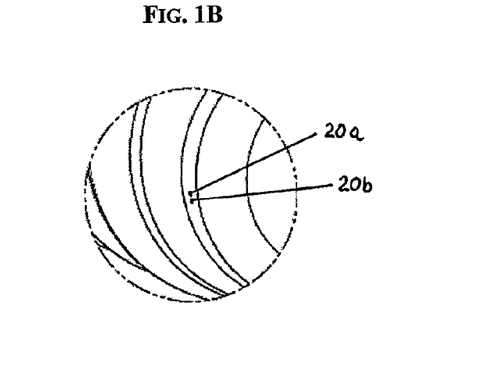
FIG. 1B is an enlarged perspective view of a distal end of the bone penetrating device of FIG. 1A, showing windows formed in threads of the bone penetrating device to allow light from an optical waveguide to illuminate tissue and to allow reflected light from the tissue through the window to be used to determine the optical characteristics of the tissue.
Figure 1C:
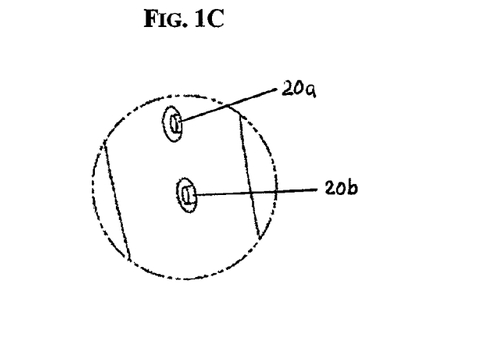
FIG. 1C is an enlarged perspective view of a thread of the bone penetrating device of FIG. 1B, showing the windows in more detail.
Figure 1D:
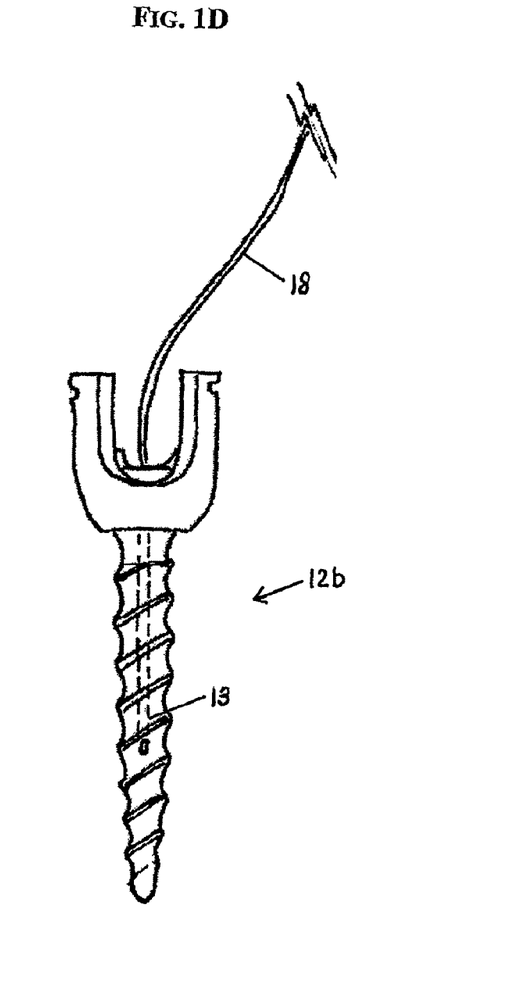
FIG. 1D is a side view of the bone penetrating device of FIGS. 1A-C, showing the optical fiber inserted through the bone screw.

The bone navigation device 11 can have a variety of configurations, but in the illustrated embodiment, it includes a handle 14 formed on or coupled to a proximal end 12p of the bone penetrating member 12. The handle 14 can have any shape and size but it is preferably adapted to facilitate grasping and manipulation of the device 10. The handle 14 can also be sized and shaped to contain electronic components for a spectroscopy system or an adaptor to attach the device 11 to a spectroscopy system. As shown in FIG. 1A, the handle 14 has a generally spherical configuration. A person skilled in the art will appreciate that any handle 14 can be fixedly or removably coupled to the bone penetrating member 12, integrally formed with the bone penetrating member 12, or that the bone navigation device 10 can be used without a driver and/or handle 14.

The bone penetrating member 12 can also have a variety of configurations, and it can be flexible or rigid depending on the intended use. In one exemplary embodiment, the bone penetrating member 12 is in the form of a bone implant and a driver for implantation of the bone implant. In the illustrated embodiment, the bone penetrating member 12 is in the form of a cannulated bone screw 12b and a driver 12a. A person skilled in the art will appreciate that the bone implant can have a variety of forms, including bone fasteners, anchors, and various non-threaded members such as a post. The bone screw 12b is removably coupled to a distal end of the driver 12a, which is adapted to drive the bone screw 12b into bone. The driver 12a can be removably coupled to the bone screw 12b using various mating techniques. For example, the driver 12a can positively engage the bone screw 12b, or the driver 12a can apply a force to the bone screw 12b to drive it into bone. A person skilled in the art will appreciate that the driver 12a can couple to the bone screw 12b in any way that allows the driver 12a to drive the bone screw 12b into bone. The bone penetrating member 12 preferably has a length that allows a distal end 12d of the bone penetrating member 12 to be positioned adjacent to a bone to be imaged, while a proximal end 12p of the bone penetrating member 12 remains external to the body. This length allows the bone penetrating member 12 to extend from the tissue surface to the imaging site, e.g., within the bone, such as the pedicle of a vertebrae. A person skilled in the art will appreciate that the bone penetrating member 12 can be made from a variety of biocompatible materials that have properties sufficient to enable the bone penetrating member 12 to be inserted into the body.

Figure 1E:
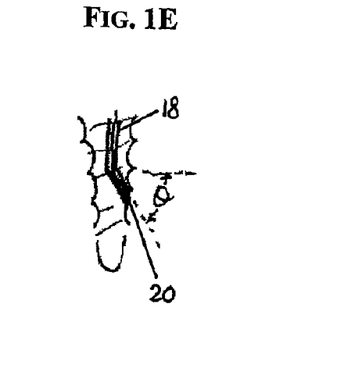
FIG. 1E is a side view of a distal end of the bone screw of FIG. 1D, showing the window in more detail.

As indicated above, the bone penetrating member 12 can also include a window 20 formed therein that can be configured to allow light from the optical waveguide 18 to pass through the window to illuminate the bone and to allow the reflected light from the bone to pass through the window and back to the optical waveguide 18. The particular location and size of the window 20 can vary depending on the type of tip 16 of the bone penetrating member 12 and the type of tissue being illuminated. In other words, the window 20 can placed at any location on the bone penetrating member 12 in order to illuminate tissue at various insertion depths. In one exemplary embodiment, the window 20 can be located in the bone penetrating member 12 at its widest part. In addition, there can be any number of windows 20 formed in the bone penetrating member 12 to accommodate any number of optical waveguide 18, or to allow imaging at more than one location on the bone. For example, multiple windows spaced a distance apart along the length can be used to indicate the bone type at different depths. The window 20 can also be in any form that allows the emitted light from the optical fiber 18 to pass through to the bone and the reflected light from the bone to pass through back to the optical waveguide 18. For example, the window 20 can be in the form of an opening extending through the bone penetrating member 12, or the window 20 can have a film or lens disposed over an opening. In the embodiment shown in FIGS. 1A-E, the window 20 is formed in the bone screw 12b that is adapted to be implanted into bone. The window 20 that allows the light from the optical waveguide(s) 18 to illuminate the surrounding tissue can be formed in a variety of locations along the length of the bone screw 12b, but in the illustrated embodiment, two windows 20a, 20b are formed between the threads of the bone screw 12b, as shown in more detail in FIGS. 1B-C. The light emitted from the distal end of the optical waveguide 18 can be angled to allow the emitted light to illuminate the area surrounding the window 20. This can be achieved in a variety of ways. For example, as shown in FIG. 1E, the distal end of the optical waveguide 18 can be angled to allow the light to pass through the window 20. A person skilled in the art will appreciate that this can be achieved using a variety of other techniques, such as a prism or angled mirror positioned within the bone penetrating member 12 at a location adjacent the distal end of the optical waveguide 18 and the window 20 to angle the light emitted from the optical waveguide 18 through the window 20. A person skilled in the art will appreciate that the windows 20a, 20b can be formed anywhere along the length of the bone screw, including on the threads. A person skilled in the art will appreciate that the window(s) can have various configurations and can be at a variety of locations on the tip or the bone penetrating member 12.

Additionally, the addition of a so-called "cosine corrector" can be added to the receiving fiber and/or the window. The purpose of a cosine corrector is to gather light traveling at angles typically outside the numerical aperture of the optical waveguide 18. In this way, the optical waveguide 18 is able to collect more light from the tissue for subsequent analysis.

In order to deliver light through the window to illuminate bone, the optical waveguide 18 extends through the optical channel formed in the bone penetrating member 12 and the tip 16 to the window 20 formed in the tip 16 and it is adapted to transmit energy from a light source at a proximal end 18p of the optical waveguide 18. The optical waveguide 18 can be fixed or removable from the optical channel and the tip 16 depending on the intended use. In the embodiment shown in FIGS. 1A-E, the optical waveguide 18 can be removably inserted through an optical channel 13 formed through the bone screw 12b to allow the optical waveguide 18 to illuminate the bone surrounding the bone screw, and then to be removed from the bone screw 12b when the bone screw 12b is implanted into bone. For example, after the bone screw 12b is implanted into bone, the optical waveguide 18 can be removed from the bone screw 12b and the driver 12a by pulling on the optical waveguide 18 and causing the optical waveguide 18 to slide through the optical channel 13 and out the proximal end 12p of the bone penetrating device 12. In use, the energy is delivered along the length of the optical waveguide 18 to a distal end of the optical waveguide 18 positioned at the window 20 formed in the tip 16. The light is emitted from the distal end 18d of the optical waveguide 18 and delivered to illuminate tissue in the immediate vicinity of the window 20. An optical waveguide is used to conduct photonic energy into the tissue of interest. Although various types of optical waveguides can be used, in an exemplary embodiment, the optical waveguide 18 is a solid-core optical fiber with cladding that conducts light using near complete internal reflectance. Alternative embodiments could involve direct tissue illumination by a light source and measurement of the reflected or transmitted light by a local charge-coupled device tuned to the appropriate wavelengths of light. The location of the light source and/or light detection device within the bone penetrating device can be problematic due to size and safety constraints. The optical waveguide 18 can be flexible or rigid depending on its intended use, and the optical waveguide 18 can be positioned within an optical channel extending through the entire length of the bone penetrating member 12 to the distal end 12d. The optical waveguide 18 can be formed from a variety of materials, including glass, quartz, polymeric materials, or any other materials which can conduct light energy. By way of non-limiting example, one suitable optical waveguide 18 is an optical fiber manufactured by Corning Incorporated (Corning, N.Y.) or Precision Optics Incorporated (Gardner, Mass.). In addition, any number of optical waveguide 18 can be used to illuminate the tissue and gather the reflected light from the tissue that has been illuminated. For example, in an exemplary embodiment, the bone navigation device can utilize first and second optical waveguides. The first optical waveguide can be positioned at a first window and used to carry the light from a light source to the tissue and illuminate the tissue, and the second optical waveguide can be positioned at a second window and used to gather the light reflected from the illuminate tissue. A person skilled in the art will appreciate that this configuration of optical waveguides and windows is merely exemplary and any configuration of optical waveguides and windows can be used. For example, each of the first and second optical waveguides can be used to both transmit and collect reflected light from each window. In an exemplary embodiment, the optical waveguides have a proximal end 18p adapted to couple to a light source, as will be discussed in more detail below, and a distal end 18d adapted to illuminate tissue and/or gather reflected light from the illuminated tissue. In use, the optical waveguide 18 can conduct light energy in the form of ultraviolet light, visible light, near infrared, infrared radiation, or coherent light, e.g., laser light. In addition, the optical waveguide 18 can also optionally function as an imaging device, such as a camera, to provide a visual image of the bone and surrounding tissue through which the bone penetrating member 12 is being passed.

In order to determine the optical characteristics of the tissue which has been illuminated by the optical waveguide, the bone navigation system 10 can also include a processor 22 adapted to collect and process data from the optical waveguide 18 for determining the optical characteristics of tissue from which the light is reflected. For example, the processor 22 can compare the reflected light from the illuminated tissue to known optical characteristics of different types of tissue to determine the type of tissue positioned in the immediate vicinity of the window 20. The processor 22 can be any standard component know in the art. In an exemplary embodiment, the processor includes a computer to compare the predetermined wavelengths of different types of tissue to the wavelength of the light reflected from the illuminated tissue and determine the type of tissue that was illuminated. A display screen can be used for displaying various types of information, including spectral characteristics of the reflected light or the determination of the type of tissue. One or more control devices in the form of, for example, buttons or knobs disposed on the processor, can be used to activate the light source to order to transmit light along the optical waveguide 18 in order to illuminate the tissue.

The bone navigation system 10 can also optionally include a signaling mechanism 24 that is adapted to provide a signal that indicates when the window 20 is positioned adjacent to a certain type of tissue. The signaling mechanism 24 can have a variety of configurations. For example, the signaling mechanism 24 can be an LED or other light source disposed on the handle 14, or an audible mechanism that indicates to a user when the window 20 is positioned adjacent to a particular type of tissue. For example, the LED can light up when an appropriate bone type is located, or it can remain lit until the bone penetrating device is no longer positioned adjacent to a particular bone type. For example, the signaling mechanism 24 can be used to indicate a type of bone that is needed for implantation of various implants. In another exemplary embodiment, the signaling mechanism 24 can include multiple indicators, such as multiple LEDs, for each type of tissue. For example, each LED could be of a different color to indicate the different tissue types. The signaling mechanism 24 can also be positioned at any location on the bone penetrating device 12 as long as the signaling mechanism 24 can be communicated to the user when the distal end of the bone penetrating device 12 is inserted into the body. For example, an LED can be positioned on a proximal portion of the bone penetrating device 12 to allow the LED to be seen by the user when the device is inserted into the body. A person skilled in the art will appreciate that any mechanism can be used to indicate when certain bone types are located. For example, the signaling mechanism 24 can include a light, a sound, a vibration, or any combination of these or other mechanisms. A person skilled in the art will also appreciate that the signaling mechanism 24 does not have to be located on the bone penetrating device at all, but rather can be a component of the processor 22 or a separate mechanism that is adapted to provide a signal the user.

Figure 2A:
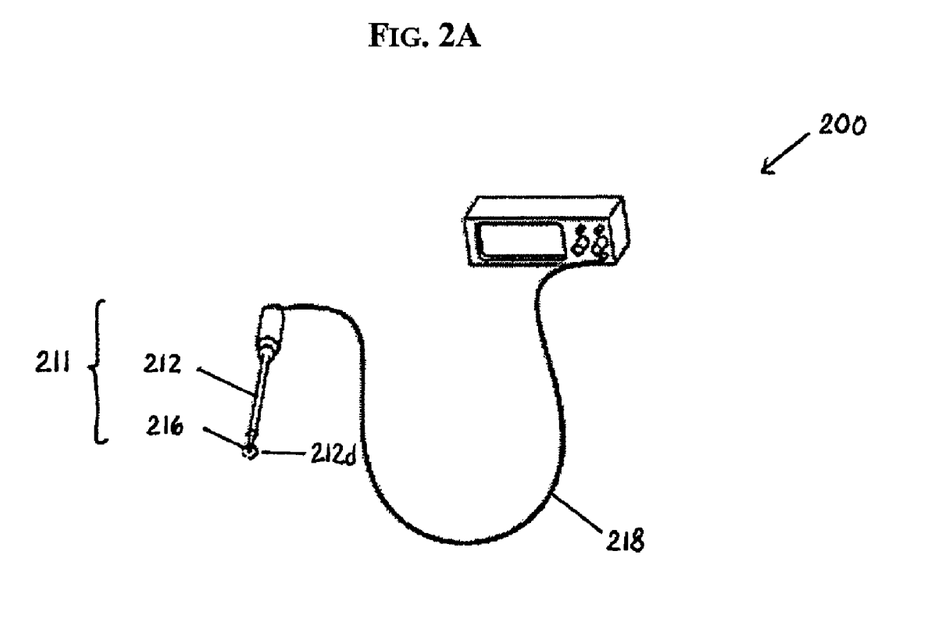
FIG. 2A is a perspective view of another embodiment of a bone navigation device having a bone penetrating device in the form of a cannulated awl.
Figure 2B:
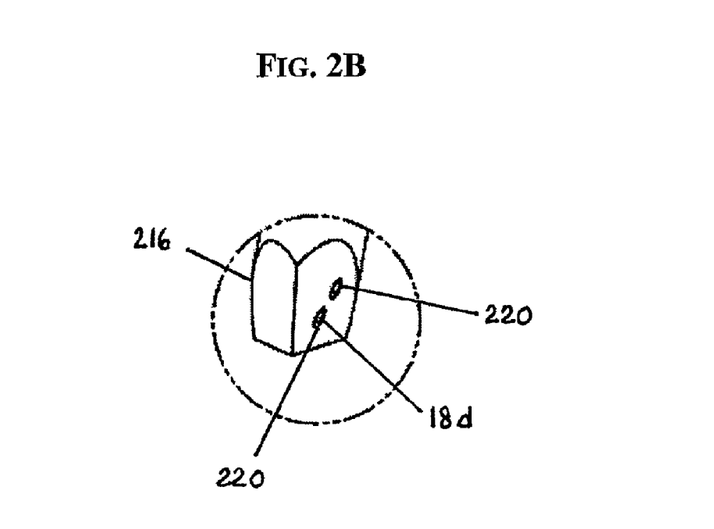
FIG. 2B is an enlarged perspective view of a distal end of the bone penetrating device of FIG. 2A, showing windows formed in the bone penetrating device to allow light from an optical waveguide to illuminate tissue and to allow reflected light from the tissue through the window to be used to determine the optical characteristics of the tissue.

As indicated above, various bone penetrating members can be used with a bone navigation device to determine the optical characteristics of tissue, thus facilitating navigation through bone. FIGS. 2A-B illustrate another exemplary embodiment of a bone navigation system 200 that is similar to the one shown in FIGS. 1A-E except that the bone penetrating member 212 is in the form of an awl that is adapted to form a bone tunnel in bone. The bone penetrating member 212 is in the form of a generally elongate shaft having a distal tip 216 formed on a distal end 212*d* and adapted to start and form a hole in bone. The tip 216 can have a variety of configurations. For example, the tip 216 can have one or more beveled surfaces adapted to facilitate the formation of the hole into bone. The bone penetrating member 211 can also include an optical channel (not shown) formed therein and adapted to house the optical waveguide(s) 218 which extend therethrough. In this embodiment, the bone penetrating member 212 includes first and second windows 220 that are located in the tip 216 on one of the beveled surfaces of the tip 216. As a result, the windows 220 are oriented at an angle relative to the axis of the bone penetrating member 212 so as to allow the optical waveguide(s) 218 access to the bone.

Figure 3A:
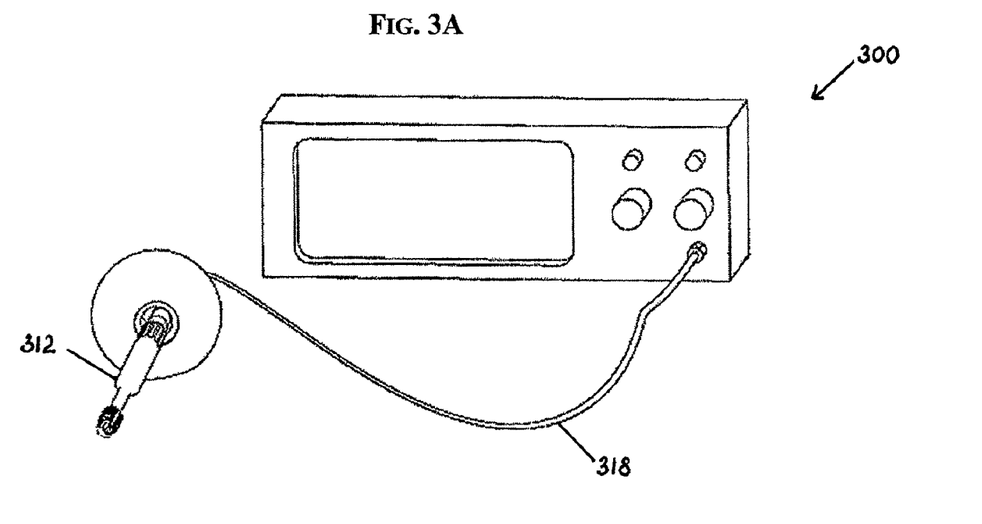
FIG. 3A is a perspective view of another embodiment of a bone navigation device having a bone penetrating device in the form of a cannulated bone tap.
Figure 3B:
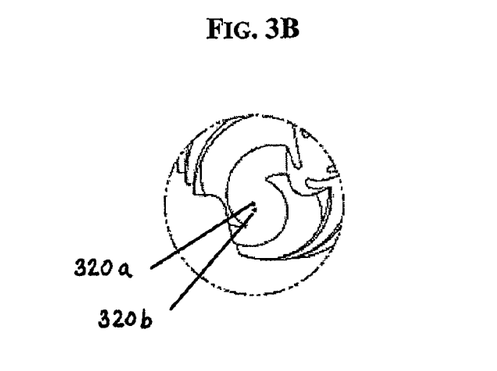
FIG. 3B is an enlarged perspective view of a distal end of the bone penetrating device of FIG. 3A, showing windows formed in a tip of the bone penetrating device to allow light from an optical waveguide to illuminate tissue and to allow reflected light from the tissue through the window to be used to determine the optical characteristics of the tissue.
Figure 3C:
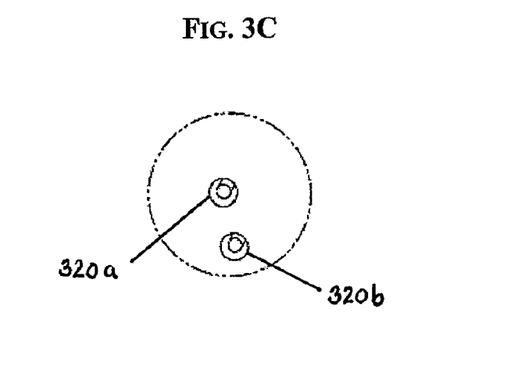
FIG. 3C is an enlarged perspective view of the tip of the bone penetrating device of FIG. 3B, showing the windows in more detail.

FIGS. 3A-C illustrate yet another exemplary embodiment of a bone navigation system 300 that is similar to the one shown in FIGS. 1A-E except that the bone penetrating device 312 is in the form of a cannulated bone tap. In this embodiment, the bone tap includes an enlarged threaded head formed at a distal end of the bone penetrating device 312 that is adapted to form a threaded hole in bone. The windows 320*a*, 320*b* to allow the light from the optical waveguide(s) 318 to illuminate the surrounding tissue can be formed in a variety of locations along the length of the bone tap, but in the illustrated embodiment the windows 320*a*, 320*b* are formed in a distal-most end of the bone tap, as shown in more detail in FIGS. 3B-C. As the windows 320*a*, 320*b* are formed at the distal-most end of the tap, the composition of the layers of tissue can be determined as the tap penetrates the bone and the threaded bone hole is formed. This can allow the threaded bone hole to be formed having a desired depth and into a desired bone type. In one exemplary embodiment, the optical waveguide(s) 318 will illuminate and interrogate the surrounding tissue for each rotation of the bone penetrating device 312. For each turn of the bone tap, a helix of the area in the immediate vicinity of the windows 320*a*, 320*b* will be illuminated, so as the bone tap is rotated and penetrated into the bone, the tissue type can be determined, i.e., if the area in the vicinity of the windows is marrow, soft tissue, or pedicular or cortical bone.

A person skilled in the art will appreciate that the bone penetrating devices shown in FIGS. 1A-3C are merely exemplary and that the bone penetrating device can be any device that is adapted to be inserted into bone. For example, the bone penetrating device can be a bone tap, drill, awl, any implant, a bone vibratome blade, a surgical probe, a cannula, etc. Moreover, a person skilled in the art will appreciate that any of the features described above with respect to one embodiment can be used with any of the embodiments of the invention.

In use, the various bone navigation systems can be inserted through tissue, or through an access port disposed in tissue, so that the handle 14 can extend from the tissue or port on the outside, and the distal end of the bone navigation systems, i.e., the tip of the bone penetrating member, can be positioned within a bone to be imaged. The bone navigation device can be positioned such that the window(s) will allow the optical waveguide(s) to illuminate the surrounding tissue, as indicated in step 400 of FIG. 4. In one exemplary embodiment, the bone penetrating member, and thus the window can be moved relative to the target bone in a variety of directions to allow an area of tissue to be scanned to obtain the optical characteristics of the tissue. This can be used, for example, to determine an appropriate location to insert an implant, such as a pedicle screw, into the bone. For example, the bone penetrating member can be rotated axially and/or moved longitudinally along its axis relative to the target bone in order to determine the optical characteristics of the tissue at various locations around and along the depth of the bone hole. After the reflected light is analyzed by the processor, as will be discussed in more detail below, the optical characteristics of the tissue can be used for various purposes, such as to determine the placement of an implant to be implanted into the bone.

Figure 4:
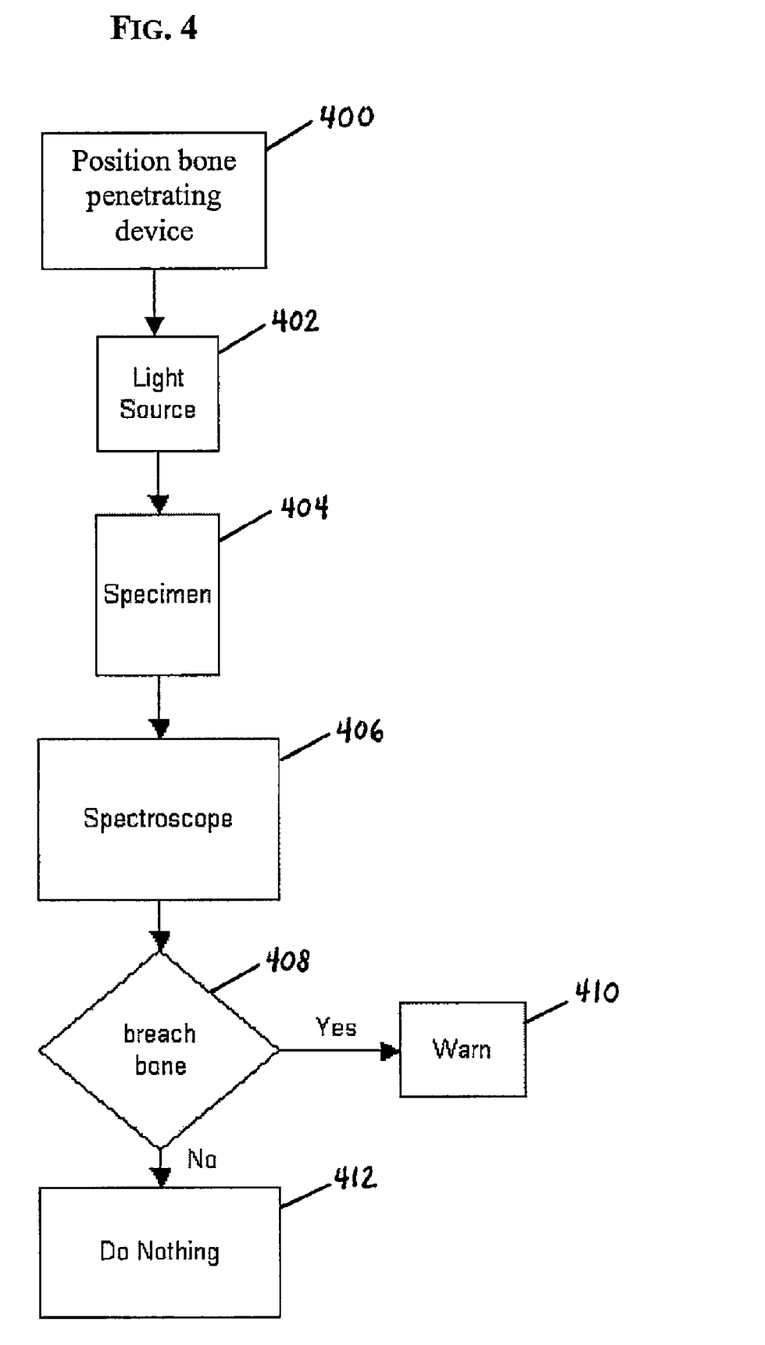
FIG. 4 is a flowchart illustrating a method for navigating bone.
Figure 6:
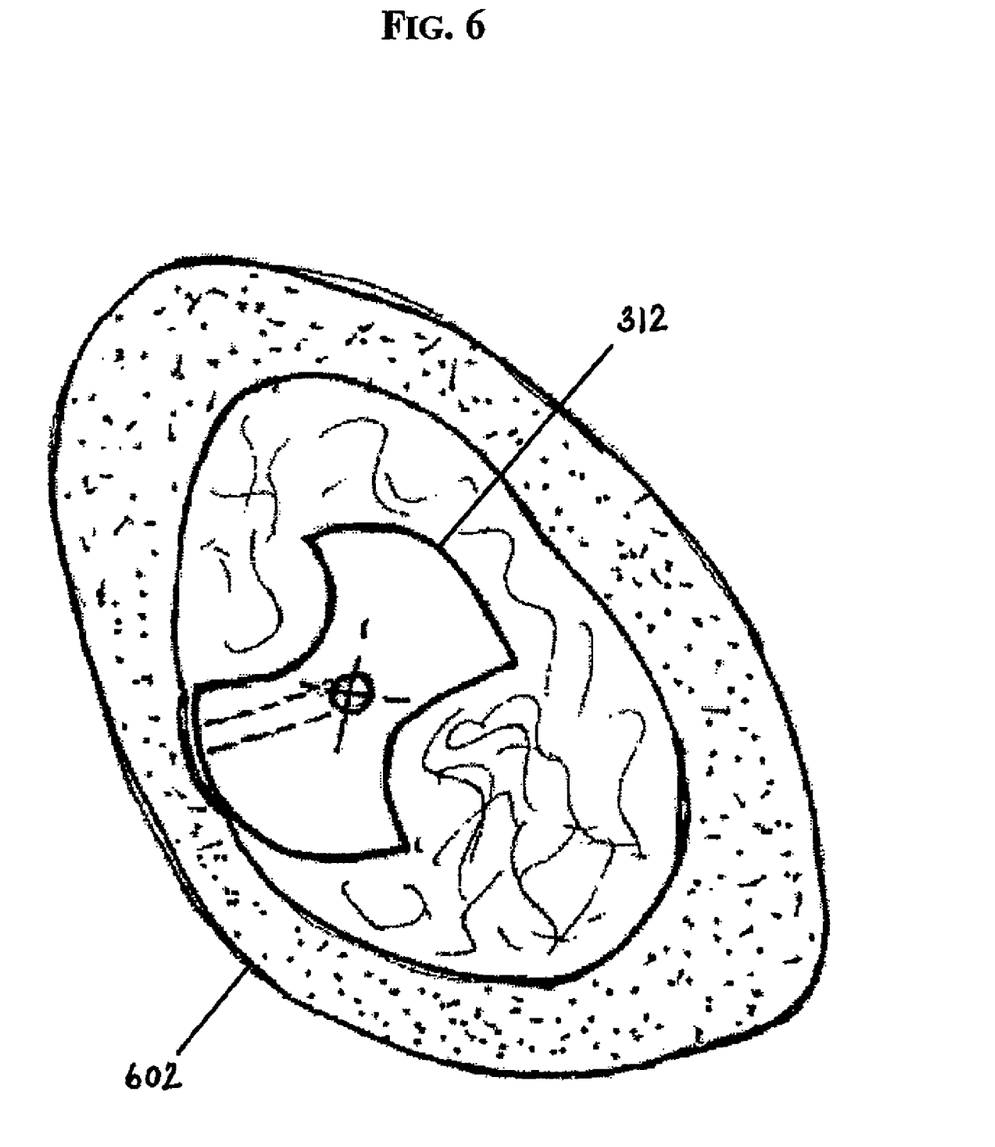
FIG. 6 is a cross-sectional view of a bone navigation device inserted into bone.
Figure 7:
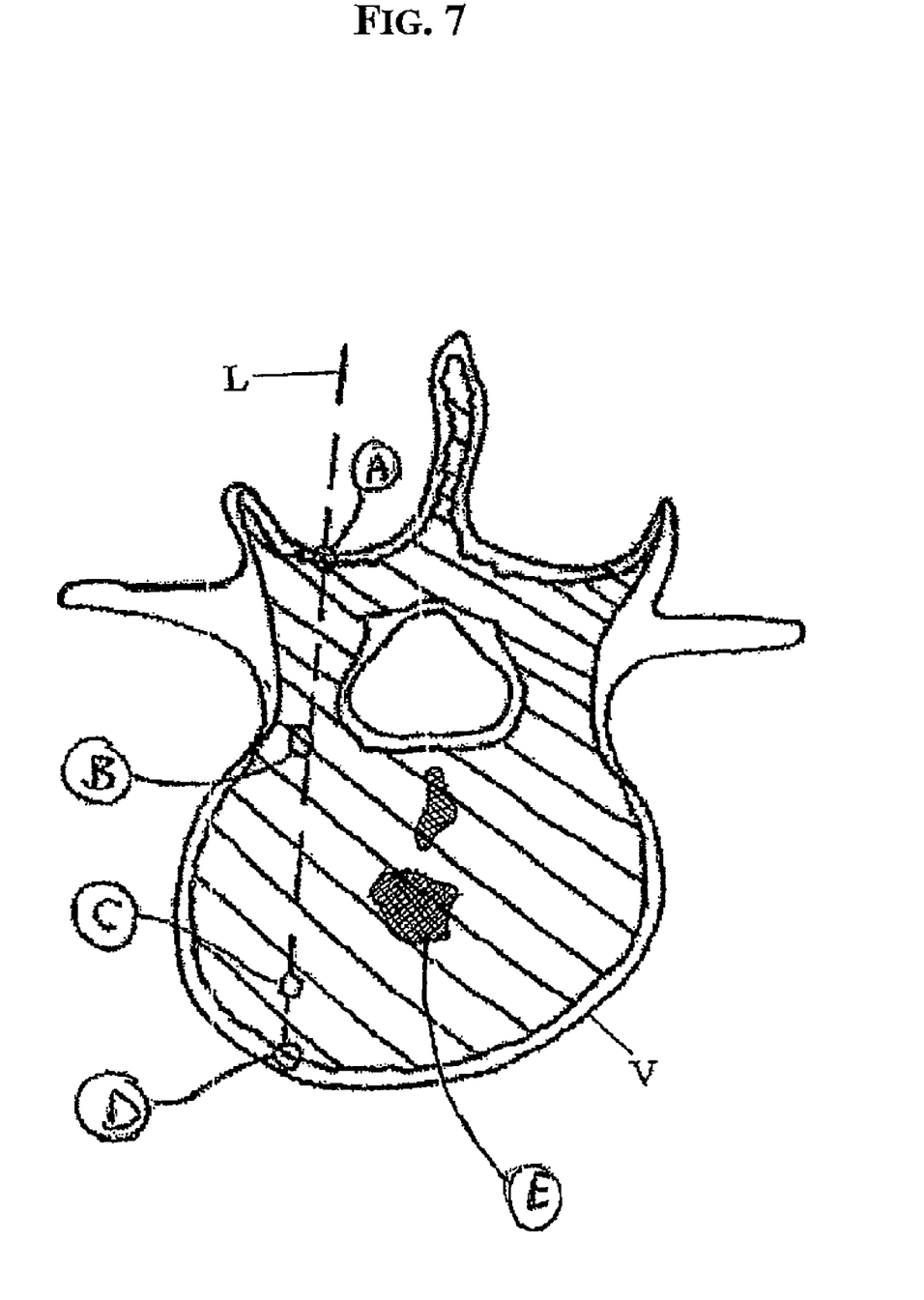
FIG. 7 is a cross-sectional view of a pedicle of a vertebra indicating the various types of bone contained therein.

To obtain the information used to determine the optical characteristics, the optical waveguides must be activated to illuminate the target tissue, as indicated in step 402 of FIG. 4. For example, the light travels along the optical fiber through the core of the fiber by constantly reflecting off the cladding of the fiber from the proximal end to the distal end of the optical fiber. As indicated above, the distal end of the optical waveguide is positioned adjacent the window to allow the light from the optical waveguide to illuminate the target bone as well as surrounding tissue, as indicated in step 404 of FIG. 4. The light that is reflected back from the illuminate tissue is collected by the optical waveguide and transmitted to the processor to analyze the reflected light to determine the optical characteristics of the tissue. This can be achieved using a spectroscope, as indicated in step 406 of FIG. 4, which can be used to produce spectral lines from the reflected light and to measure its wavelengths and intensities. For example, in order to determine an acceptable location into which an implant can be implanted into the target bone, the information from the spectroscope can be analyzed by the processor to determine if this location is acceptable or if implantation of the implant would present a problem, such as implantation into the wrong type of bone, or if a bone breach would occur, as indicated in step 408 of FIG. 4. For example, FIG. 6 illustrates the bone penetrating device 312 as shown in FIG. 3A penetrating bone. As seen, the bone penetrating device 312 is adjacent to a wall 602 of a pedicle in a vertebrae. The processor 22 can achieve this analysis using a variety of techniques generally known in the art. In one exemplary embodiment, the processor 22 can include one or more databases containing information about the characteristics, such as the spectral characteristics, of different types of tissue. This information stored in the databases can be compared to the spectral information from the light reflected back from the tissue to determine the optical characteristics of the target bone. For example, FIG. 7 illustrates a cross-section of a vertebra V indicating the various types of bone contained therein. The various types of bone can be illuminated with the optical fibers to differentiate between them to determine the appropriate location to implant a bone implant. The line L indicates a trajectory of a bone penetrating device as it navigates the vertebra V. As the bone penetrating device moves from point A to D, the bone navigation system determines that the bone located at points A and D are cortical bone shell, and the bone located at points B and C are trabecular bone core. In one embodiment, an appropriate location for implantation of a bone implant would be located at point D without breaching the cortical shell.

One condition that is detectable by spectroscopic analysis of local tissues is the presence of a vascular sinus E. As there is no trabecular bone in vascular sinus E, placement of a threaded screw or cantilevered post would result in a mechanically comprised situation. Similarly, this location would be inappropriate for an injectable implant, such as vertebroplasty cement, since there is the potential to create a vascular embolism.

Figure 5:
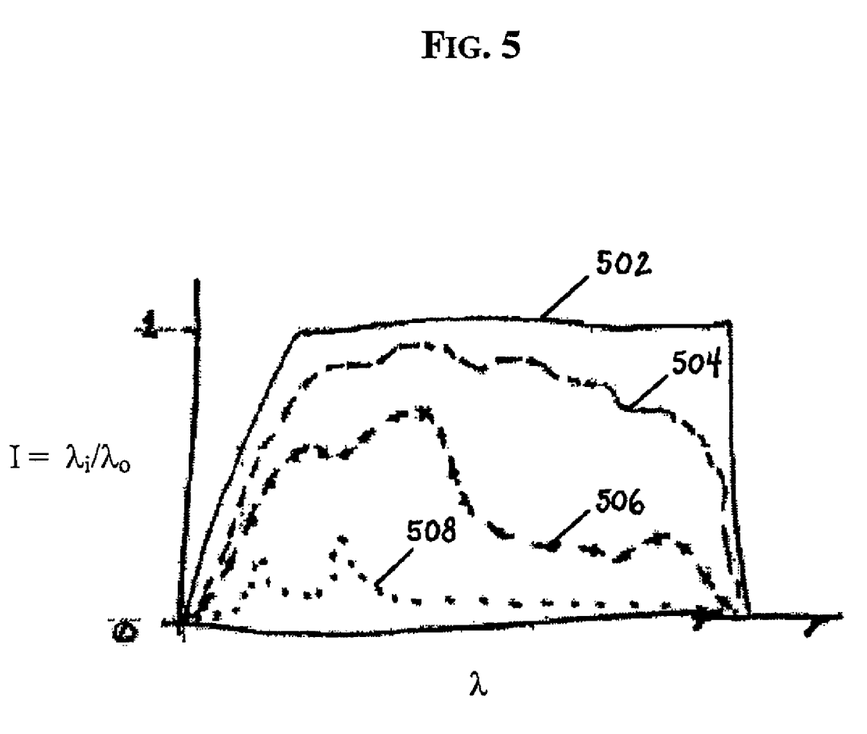
FIG. 5 is a graph showing the spectral characteristics of various types of tissue.

As noted above, in one exemplary embodiment, information stored in the databases can include the spectral characteristics of various types of bone and tissue, including cortical bone, bone marrow, trabecular bone, soft tissue, neural tissue, and non-bone tissue. The optical characteristics of cortical bone are that cortical bone is very light scattering due to calcium crystals contained therein. Cortical bone has a high collagen content and very little vasculature. These features indicate a definite transition from bone to other types of tissue. The spectral characteristics of marrow are that marrow is very light scattering and highly light absorbent. The spectral characteristics of soft tissue are that soft tissue transmits significantly more light than bone or marrow. These differences in the different types of bone and tissue allow a comparison between the information stored in the databases and the reflected light collected by the optical waveguides to be used to determine the optical characteristics of the area surrounding the window formed in the bone penetrating device. FIG. 5 illustrates a graph of the spectral characteristics of bone, marrow, and soft tissue as represented by the relative intensity for various wavelengths of light, I, where $I=\lambda_i/\lambda_o$, and $\lambda_i$ is the wavelength of the measured tissue or bone intensity and $\lambda_o$ is the wavelength of the measured optical input. Line 502 represented the reference line of $\lambda_o/\lambda_o$. Line 504 represents the I of bone, as bone absorbs very little light. Line 506 represents the I of soft tissue, as soft tissues transmits light, and line 508 represents the I of marrow, as marrow is highly absorbent of light.

The processor can then perform a comparison between the spectral information regarding the reflected light from the target tissue and the information stored in the one or more databases to determine the type of tissue surrounding the device, and optionally whether or not this type of bone is an acceptable location for which to implant a component into the bone. If this location is not acceptable for an implant, the bone navigation device can warn the user, such as with the signaling mechanism discussed above and as indicated in step 410 of FIG. 4. If a bone breach or other problem will not occur, no warning is issued, as indicated in step 412. A person skilled in the art will appreciate that a signal could be issued instead to indicate an acceptable location while no warning is given if a breach is possible. Moreover, a different signal could be given for both situations to indicate to the user the status of the target bone. This process is repeated as the bone penetrating device is navigated, e.g., repositioned radially and/or longitudinally, within the target bone.

In an exemplary embodiment, bone autofluorescence is used to detect location and quality of bone for the placement of a bone penetrating device. Hydroxy-apatite calcium crystals within ossified tissues transform light at 488 nm into light at greater than 515 nm wavelength. Theoretically, a higher calcium crystal concentration would result in more auto fluorescence. Theoretically, absence of autofluorescence indicates illumination of non-ossified tissues (as indicated by the absence of calcium crystals that create the autofluorescent condition). In this particular application, monochromatic light with a wavelength of 488 nm can be sent along the optical waveguide to illuminate the surrounding tissue. The tissue can reflect back light at a wavelength of greater than 515 nm, along with backscattered light at 488 nm. In such an application of the invention being disclosed, the light source could be reduced to a single LED (488 nm) and a simple high-pass filtered light receiving system (passing light at wavelengths greater than 515 nm). This information can be used by the spectroscope and the processor to determine the type of the tissue which was illuminated. Based on data stored in the processor, the bone navigation device will either warn the user that the current location being analyzed is not the type of bone into which an implant can be implanted, i.e., when there is none or little light reflected back that is greater than 515 nm, or will present no warning, i.e., when there is light reflected back with a wavelength of greater than 515 nm. Thus, a user knows that the current location being analyzed is an appropriate location to implant a component into bone. For example, the bone can be analyzed to determine an appropriate location for implanting a bone screw. After the optical characteristics of the surrounding tissue are identified, the appropriate location can be determined, and a bone screw can be implanted into bone using a driver to drive it through the bone.

There are also potential diagnostic uses for the present invention in addition to the navigation of bone as described above. For example, the presence or absence of an expected optical/spectral tissue feature can have various diagnostic uses, such as the presence of autofluorescence but absence of oxygenated hemoglobin (measure by light absorption at 550 nm) can indicate ischemic bone (or at least hypoperfused bone). Similarly, the presence of light absorption at 930 nm (NIR range) indicates the presence of lipids (fat). In bone marrow, conversion of red marrow to "yellow marrow" is achieved by replacement of hematopoetic marrow with adipose tissues and this condition precedes several bone disease conditions. In addition, optical signal enhancement can be achieved with the addition of dyes and/or tissue clearing agents to assist light penetration, decrease light scatter, enhance light absorption, create a photochemical reaction, or induce a photobiological effect. The signal can also be modified by the displacement of soft tissues within the bone (such as clearing of the marrow and replacement by another material like bone cement, PMMA, bone wax, saline, etc.). Such a technique can allow a "whole tissue signal" to be gathered. Then some tissue components could be removed via lavage to allow a "cleared tissue signal" to be gathered and compared to the "whole tissue signal" for additional analysis. Similarly, transient photonic events could be employed such as fluorescence recovery after photobleaching (FRAP) that describe recovery of a molecule or feature or tissue component after a "bleaching" procedure where the molecule, feature, or tissue component was removed. Additionally, the photonic spectroscopic signal could be combined with various physical and chemical signals to enhance the spectroscopic algorithm. Temperature, chemical concentrations, enzyme reaction rates, etc. could provide the signals required for additional analysis. Fabry-Perot grated fiber optics with interferometers and grated chemical sensitive coatings would enable such an embodiment. Chemical reactions that occur within the fiber coatings create a color shift in the grated coating that is measured by the light passing through the fiber. The color shift in the light corresponds to either a local chemical reaction rate, enzyme concentration, or chemical concentration. For example, such a device is commercially available by Ocean Optics Incorporated (Dunedin, Fla.).

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, and any other material that is biologically compatible and non-toxic to the human body.

One skilled in the art will appreciate further features and advantages based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A bone navigation device, comprising:
   a bone screw having a rod-receiving recess and a threaded shank adapted to penetrate bone, the bone screw having at least one optical waveguide extending therethrough and configured to emit light in the visible to near infrared range to illuminate bone and receive reflected light from the bone;
   a plurality of windows formed in a sidewall of the threaded shank of the bone screw adapted to allow light from the at least one optical waveguide to illuminate the bone; and
   a processor configured to collect data from the at least one optical waveguide and to determine optical characteristics of the bone from which the light is transmitted or reflected;
   wherein the plurality of windows are spaced along a length of the shank such that when the bone screw is inserted in bone, the windows are positioned at different depths.

2. The device of claim 1, wherein the at least one optical waveguide comprises first and second optical waveguides, the first optical waveguide being configured to illuminate bone and the second optical waveguide being configured to receive light reflected from the illuminated bone.

3. The device of claim 1, wherein the at least one optical waveguide comprises an optical fiber.

4. The device of claim 1, further comprising a signaling mechanism configured to provide distinct signals based on the determined optical characteristics of the bone.

5. The device of claim 1, wherein at least one of the plurality of windows is positioned at a widest portion of the shank of the bone screw.

6. The device of claim 1, further comprising a driver removably coupled to a proximal end of the bone screw, wherein the at least one optical waveguide extends through the driver.

7. The device of claim 1, wherein the processor is configured to determine the optical characteristics of the bone by comparing a wavelength of light reflected back from the bone with known values indicating tissue composition.

8. A method of implanting a bone screw, comprising:
   driving a bone screw into bone using a driver;
   illuminating tissue surrounding a plurality of openings formed in a threaded sidewall of the bone screw with light emitted from at least one optical waveguide extending through the bone screw;
   detecting light reflected back from the tissue to determine optical characteristics of the tissue;
   repositioning the bone screw in the tissue based on the determined optical characteristics of the tissue; and
   removing the at least one optical waveguide from the bone screw through the driver.

9. The method of claim 8, wherein the light emitted from the at least one optical waveguide has a known wavelength.

10. The method of claim 9, wherein determining the optical characteristics of the tissue includes comparing a wavelength of light reflected back from the tissue with known values indicating tissue composition.

11. The method of claim 9, wherein determining the optical characteristics of the tissue includes determining whether the tissue is cortical bone, bone marrow, trabecular bone, soft tissue, neural tissue, or non-bone tissue.

12. The method of claim 8, wherein repositioning the bone screw comprises axially repositioning the bone screw to determine the composition of tissue at a plurality of depths.

13. The method of claim 8, wherein repositioning the bone screw comprises radially repositioning the bone screw to determine the composition of tissue at a plurality of locations axially surrounding the bone screw.

14. The method of claim 8, wherein a signal is generated indicating a portion of the tissue into which the bone screw can be implanted.

15. The method of claim 14, wherein a handle coupled to the driver includes an LED, and the signal involves illuminating the LED.

16. The method of claim 8, wherein a warning signal indicates a portion of the bone into which the bone screw cannot be implanted.

* * * * *